United States Patent
Kroll

(10) Patent No.: US 7,526,336 B2
(45) Date of Patent: Apr. 28, 2009

(54) LEFT HEART IMPLANTABLE CARDIAC STIMULATION SYSTEM WITH CLOT PREVENTION AND METHOD

(75) Inventor: Mark W. Kroll, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

(21) Appl. No.: 10/794,531

(22) Filed: Mar. 5, 2004

(65) Prior Publication Data

US 2005/0197673 A1 Sep. 8, 2005

(51) Int. Cl.
*A61N 1/20* (2006.01)

(52) U.S. Cl. .......................... 607/9; 607/119

(58) Field of Classification Search .............. 607/9, 607/11, 119, 121, 13
See application file for complete search history.

(56) References Cited

U.S. PATENT DOCUMENTS

| | | | |
|---|---|---|---|
| 3,512,183 A | 5/1970 | Sharp et al. | |
| 4,033,357 A | 7/1977 | Helland et al. | 128/418 |
| 4,265,928 A * | 5/1981 | Braun | 427/2.25 |
| 4,280,514 A | 7/1981 | MacGregor | |
| 4,281,668 A | 8/1981 | Richter et al. | 128/784 |
| 4,506,680 A | 3/1985 | Stokes | |
| 4,711,251 A | 12/1987 | Stokes | |
| 4,991,583 A * | 2/1991 | Silvian | 607/13 |
| 5,348,553 A | 9/1994 | Whitney | 606/41 |
| 5,496,360 A | 3/1996 | Hoffmann et al. | |
| 5,603,731 A * | 2/1997 | Whitney | 607/121 |
| 5,713,944 A * | 2/1998 | Kroll | 607/122 |
| 5,713,945 A | 2/1998 | Fischer et al. | |
| 5,902,329 A | 5/1999 | Hoffmann et al. | |
| 6,010,573 A | 1/2000 | Bowlin | 118/620 |
| 6,282,444 B1 | 8/2001 | Kroll et al. | |
| 6,317,615 B1 | 11/2001 | KenKnight et al. | 600/372 |
| 6,564,107 B1 | 5/2003 | Bodner et al. | 607/122 |
| 6,648,881 B2 | 11/2003 | KenKnight et al. | 606/32 |
| 6,980,865 B1 * | 12/2005 | Wang et al. | 607/121 |
| 2002/0147470 A1 * | 10/2002 | Weiner et al. | 607/9 |
| 2003/0130701 A1 * | 7/2003 | Miller | 607/9 |
| 2004/0098055 A1 | 5/2004 | Kroll et al. | |

FOREIGN PATENT DOCUMENTS

EP 1 424 095 A1 6/2004
WO WO 99/21613 5/1999

* cited by examiner

*Primary Examiner*—George R Evanisko
*Assistant Examiner*—Michael Kahelin

(57) ABSTRACT

An implantable cardiac stimulation device provides pacing stimulation therapy from within the left ventricle of a heart. The device includes a pulse generator adapted to be coupled to an implantable cardiac stimulation electrode and a power supply that maintains the stimulation electrode at a negative voltage. The electrode may be implanted within the left ventricle by feeding the electrode from the right ventricle through the right ventricular septum and into the left ventricle.

6 Claims, 5 Drawing Sheets

LEFT HEART IMPLANTABLE CARDIAC STIMULATION SYSTEM WITH CLOT PREVENTION AND METHOD

FIELD OF THE INVENTION

The present invention generally relates to an implantable cardiac stimulation system and more particularly to such a system capable of stimulating the left heart while preventing clot formation. The present invention is more particularly directed to such a system including a lead having an electrode implantable in the blood pool of the left ventricle of the heart, wherein the electrode and lead components are treated to oppose clot formation.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads and a proximal connector carried by the leads couple the electrodes to the device to enable the device to sense cardiac electrical activity and deliver the desired therapy.

Traditionally, therapy delivery had been limited to the venous or right side of the heart. The reason for this is that implanted electrodes can cause blood clot formation in some patients. If a blood clot were released arterially from the left heart, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, or cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

Notwithstanding the advancements in left heart therapy using leads/electrodes implanted in the coronary sinus region of the heart, it would still be very desirable to alternatively be able to place a lead/electrode in the left ventricular cavity. This would enable the electrode(s) to contact the left ventricular blood pool. Such blood pool contact would lower left heart pacing thresholds and hence extend device life by requiring lower pacing outputs. It would also enable more localized sensing of left heart activity. This which would lead to better coordination of right heart side and left heart side therapy due to increased specificity in left heart activity detection.

As previously mentioned, direct access to the left heart, such as the left ventricle, has been limited due to the potential of clot formation around implanted leads and electrodes. The present invention addresses this issue by providing an implantable cardiac stimulation system capable of delivering stimulation pulses to an electrode implanted in the blood pool of the left ventricle while preventing clot formation which may be otherwise potentially occasioned by such an arrangement.

SUMMARY OF THE INVENTION

What is described herein is an implantable cardiac stimulation device comprising a pulse generator adapted to be coupled to an implantable cardiac stimulation electrode, and a power supply that maintains the stimulation electrode at a negative voltage. The pulse generator may provide a negative going stimulation pulse starting from the negative voltage or a positive going stimulation pulse starting from the negative voltage. The pulse generator and power supply together preferably provide less than an average current of 100 nano amperes.

The absolute value of the negative voltage in one embodiment is greater than 25 mV, for example on the order of 50 mV.

In another illustrative embodiment, an implantable cardiac stimulation system comprises at least one implantable lead including at least one stimulation electrode, and an implantable cardiac stimulation device comprising a pulse generator adapted to be coupled to the at least one stimulation electrode, and a power supply that maintains the at least one stimulation electrode at a negative voltage. The lead may include a conductor that couples the pulse generator and the power supply to the at least one electrode, an insulator overlying the conductor and a conductive coating overlying the insulator. The conductive coating may be coupled to a power supply to receive a negative voltage.

Alternatively, the lead may include a conductor that couples the pulse generator and the power supply to the at least one electrode, an insulator overlying the conductor, a conductive coating overlying the insulator, and a second insulator overlying the conductive coating. The device may include a second power supply coupled to the conductive coating that maintains the conductive coating at a negative voltage.

In yet another illustrative embodiment, a method of pacing the left ventricle of a heart comprises implanting a stimulation electrode in the left ventricle of the heart, applying a continuous negative voltage to the electrode, and providing pacing pulses to the electrode.

The implanting step may include feeding the stimulation electrode through the right ventricular septum into the left ventricle.

BRIEF DESCRIPTION OF THE DRAWINGS

Further features and advantages may be more readily understood by reference to the following description taken in conjunction with the accompanying drawings, in which.

DESCRIPTION OF THE PREFERRED EMBODIMENTS

The following description is of the best mode presently contemplated. This description is not to be taken in a limiting sense but is made merely for the purpose of describing the general principles of the illustrative embodiments. The scope of the invention should be ascertained with reference to the issued claims. In the description that follows, like numerals or reference designators will be used to refer to like parts or elements throughout.

Figure 1:
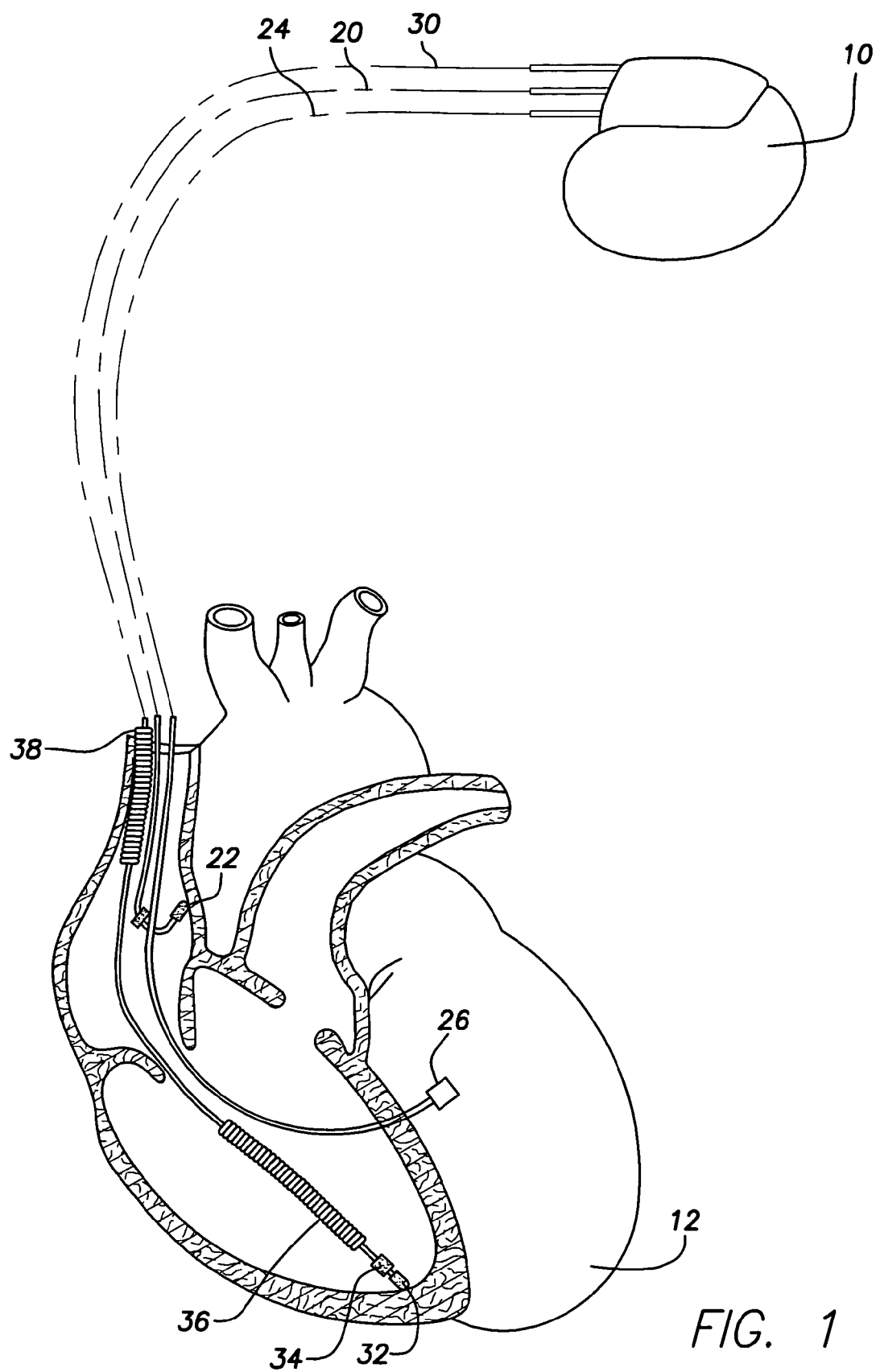
FIG. 1 is a simplified diagram illustrating an implantable stimulation device and lead system for delivering stimulation therapy to multiple chambers of a patient's heart including delivering pacing stimulation to the left ventricle.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left ventricular cardiac signals and to provide left ventricular pacing therapy, the stimulation device 10 is coupled to a lead 24 designed for placement in the left ventricle. The lead includes a left ventricular tip electrode 26 positioned in the blood pool of the left ventricle. To that end, the electrode 26 and lead 24 are fed down the superior vena cava (SVC), into the right atrium, into the right ventricle, and through the right ventricular septum into the left ventricle. As will be seen subsequently, the illustrative embodiment provides a means that prevents clot formation within the left ventricle which may otherwise potentially occur due to the presence of the lead 24 and electrode 26 within the left ventricle.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
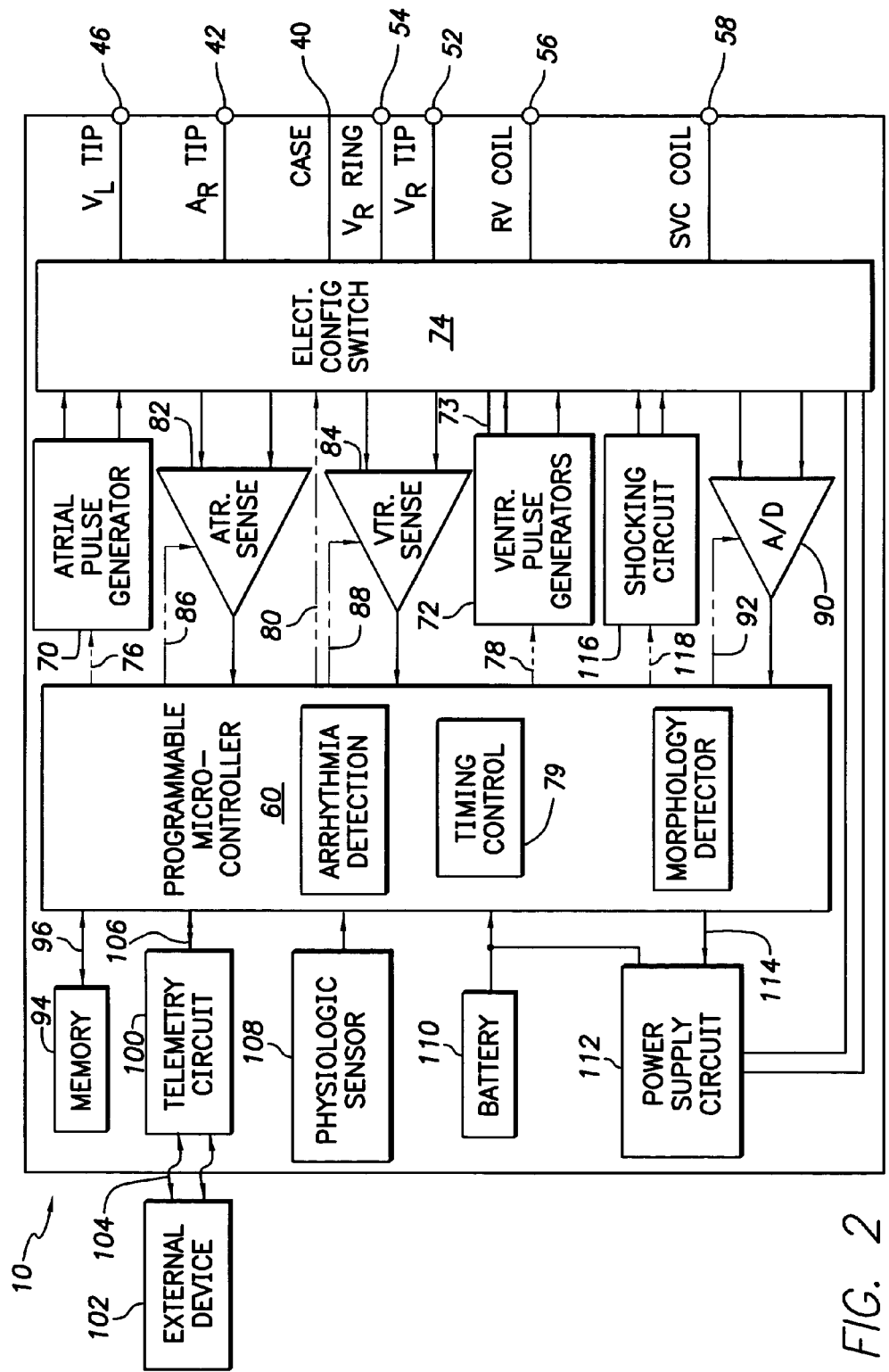
FIG. 2 is a functional block diagram of a multi-chamber implantable stimulation device according to one illustrative embodiment.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 46, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22. To achieve left chamber sensing and pacing, the connector includes at least a left ventricular tip terminal ($V_L$ TIP) 46 adapted for connection to the left ventricular tip electrode 26. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

Figure 4:
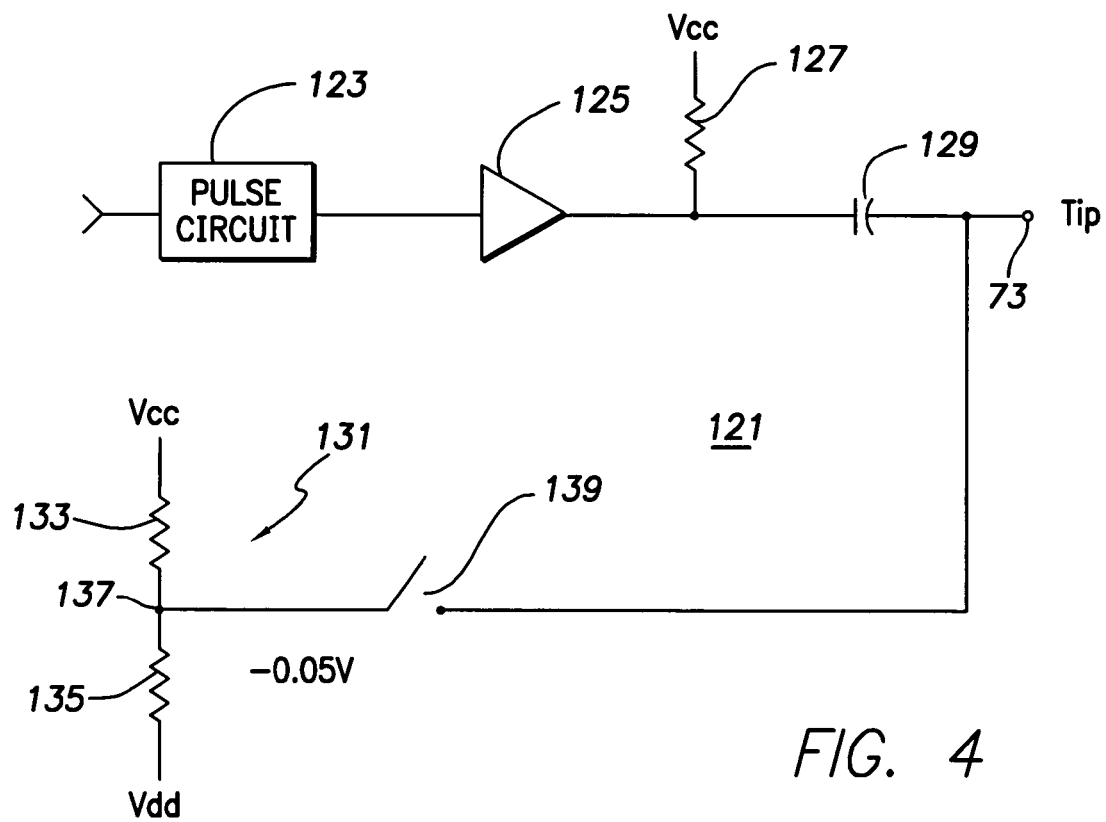
FIG. 4 is a simplified schematic block diagram of a pulse generator according to one illustrative embodiment.

As shown in FIG. 2, an atrial pulse generator 70 and ventricular pulse generators 72 generate pacing stimulation pulses for delivery by the right atrial lead 20, the right ventricular lead 30, and/or the left ventricular coronary sinus lead 24 via an electrode configuration switch 74. The ventricular pulse generators 72 preferably include at least two dedicated, independent pulse generators. One pulse generator is preferably used to pace the right ventricle while the other pulse generator, to be described hereinafter with reference to FIG. 4, is particularly configured to provide pacing therapy to the left ventricle. The left ventricular pulse generator provides its pacing pulses on output 73.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest, under the control of the microcontroller via appropriate control signals 86 and 88 respectively. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, via appropriate control signals, 76 and 78, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90, under the control of the microcontroller 60 via control signal 92, is configured to acquire intracardiac electrogram signals convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries. A simplified battery circuit will be described subsequently with reference to FIG. 3.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In accordance with at least one illustrative embodiment, the device 10 supports pacing stimulation therapy within the left ventricle. To this end, the switch 74 may be configured to provide pacing stimulation pulses from the left ventricular pulse generator output 73 to the left ventricular tip electrode 26. In order to preclude the formation of potential blood clots within the left ventricle which may potentially result by virtue of the lead 24 and electrode 26 being within the left ventricle, the device 10, in accordance with one illustrative embodiment, maintains a continuous negative voltage on electrode 26 with respect to the patient. This will reverse the passive electropositivity of the electrode metal in blood. Many different metals may be utilized as electrodes for this application. One preferred metal is platinum which has a passive electropositivity in blood of about 125 mVs. While such electrodes are inherently prothrombogeic, this process may be reversed by driving the electrode with a slight negative voltage of, for example, −50 mVs. This would be sufficient to prevent thrombus formation.

While in one illustrative embodiment the negative voltage on electrode 26 is continuously maintained, it will be apparent to those skilled in the art that the negative voltage can be applied substantially continuously, or for significant portions of the time rather than continuously. For example, applying the negative voltage for more than half the time is believed to achieve the same result, namely preventing thrombus formation. Thus, in an alternate embodiment, the negative voltage could be provided for a relatively long period of time, for example, on the order of tens of milliseconds, followed by a brief termination, for example on the order of a few milliseconds, and the process repeated. Those skilled in the art will readily contemplate various different scenarios that achieve the same result, all of which fall within the scope of the invention.

Blood solids have negative charges. A typical platelet has about $2 \times 10^6$ electronic equivalent charges, lymphocytes have a charge of approximately $10.3 \times 10^6$ and erythrocytes have a charge of about $10.3 \times 10^6$. Since these are negative charges, they are naturally attracted to any positive charge. Platinum, for example, in blood generates a positive potential of 0.125 volts. Thus, this will tend to attract blood cells. However, a negative potential as little as 50 mV or more will repulse blood cells and forestall thrombosis. Hence, preferably, the absolute value of the negative voltage maintained on the electrode 26 would be, for example, greater than 25 mVs.

As will be seen hereinafter, the left ventricular pulse generator includes a power supply which maintains a negative voltage on the electrode 26. Also, it will be noted in FIG. 2, that the device 10 includes a second power supply 112. The second power supply 112 is coupled to the battery 110 and under the control of the microcontroller 60 via control signal 114, generates a negative voltage, at low current, when needed to repulse blood cells. The second power supply 112 is of particular advantage for applying the negative voltages therefrom to conductors of the lead 24 other than the electrode 26 as will be seen subsequently.

Figure 3:
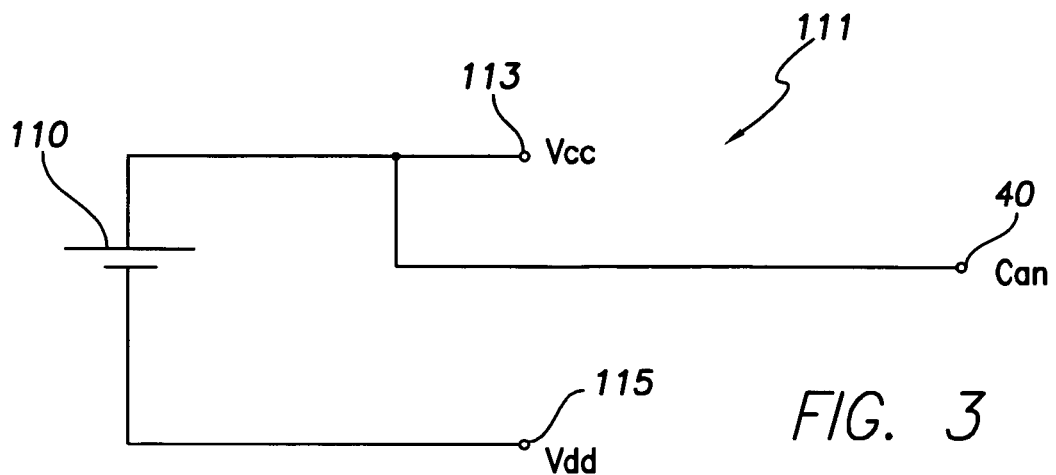
FIG. 3 is a simplified schematic diagram of the battery circuit of the device of FIGS. 1 and 2.

FIG. 3 shows a simplified diagram of a battery circuit 111 of the device 10. The battery circuit includes the battery 110. It will be noted that the positive terminal of battery 110 is coupled to a terminal 113 identified as $V_{cc}$. The negative terminal of battery 110 is coupled to another terminal 115 identified as $V_{dd}$. The case 40 or can of the device is coupled to the positive terminal of the battery 110 and thus to $V_{cc}$.

FIG. 4 shows a simplified diagram of the left ventricular pulse generator 121 according to one illustrative embodiment. The pulse generator 121 includes a pulse circuit 123 which provides low amplitude pacing pulses. The low amplitude pacing pulses are amplified by an amplifier 125. The output of amplifier 125 is coupled to $V_{cc}$ by a resistor 127. The output of amplifier 125 is also capacitively coupled by a capacitor 129 to the output 73.

It will also be noted that the output 73 is coupled to a power supply 131 of the pulse generator 121. The power supply 131 includes a first resistor 133 which is coupled to $V_{cc}$ and a second resistor 135 which is coupled to $V_{dd}$. The values of the resistors 133 and 135 are selected so that a voltage of, for example, −50 mVs appears at their common junction 137. The common junction 137 is coupled to the output 73 by a switch 139 which is closed when the device 10 is to provide left ventricular pacing with an electrode, such as electrode 26, within the left ventricle.

It will be noted from FIG. 4, that the power supply 131, when switch 139 is closed, provides a continuous negative voltage to the output 73 of the pulse generator 121. This negative voltage will be applied to the electrode 26 to provide a negative potential suitable for repulsing blood cells and for stalling thrombosis.

Figure 5:
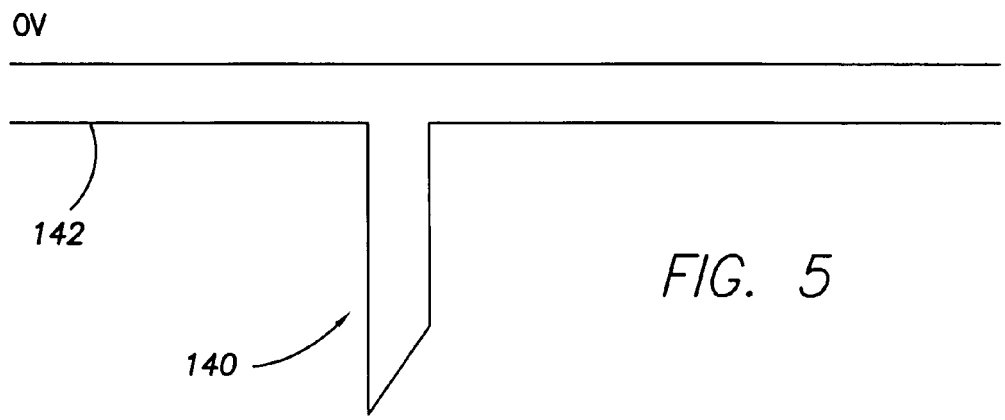
FIG. 5 is a waveform of a pacing pulse that may be applied to a left ventricle in accordance with one illustrative embodiment.

FIG. 5 illustrates a pacing pulse 140 obtainable from the pulse generator 121. It will be noted that the electrode 26 is maintained at a constant negative voltage 142 and that the pacing pulse 140 is negative going in order to maintain the negative potential on the electrode 26.

Figure 6:
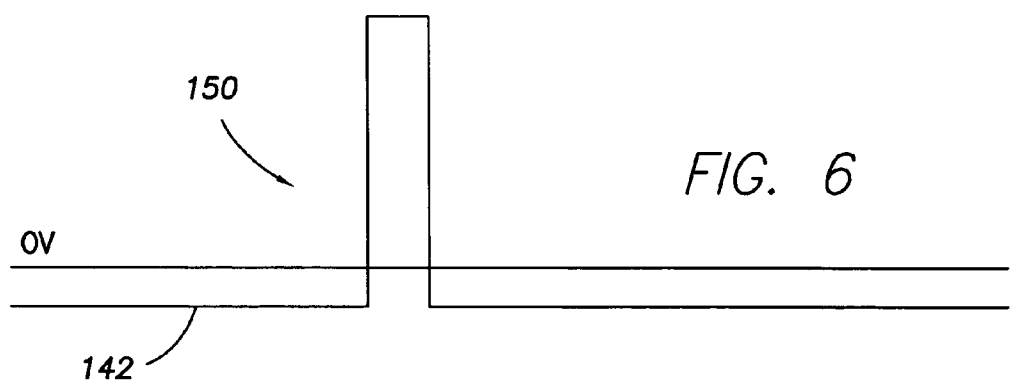
FIG. 6 is another waveform of a pacing pulse that may be applied to a left ventricle.

FIG. 6 shows an alternative pacing pulse 150. The pacing pulse 150 is positive going from the negative potential 142 otherwise constantly maintained on the electrode 126. The pacing waveform of FIG. 6 is premised upon a pacemaker specification that requires that the average DC current out of a pacemaker be less than 100 nano amps. The purpose of this specification was to prevent corrosion on stainless steel electrodes, which are now generally considered to be obsolete. However, the waveform of FIG. 6 serves to enable adherence to this specification by having the pulse generator pace anodically in a positive direction while the background voltage would remain negative. The value of the negative voltage 142, the maximum amplitude of pacing pulse 150, and the width of pacing pulse 150 may be selected so that the net average current provided at electrode 26 is near zero or within 100 nano amps of zero.

As will be understood by those skilled in the art, the exposed surfaces of the lead 24 to the left ventricular blood pool, in addition to the electrode 26, must be dealt with to preclude thrombosis. While some lead materials may be inert in this regard and thus would need no special treatment, some lead insulations may require special treatment to preclude thrombosis.

Figure 7:
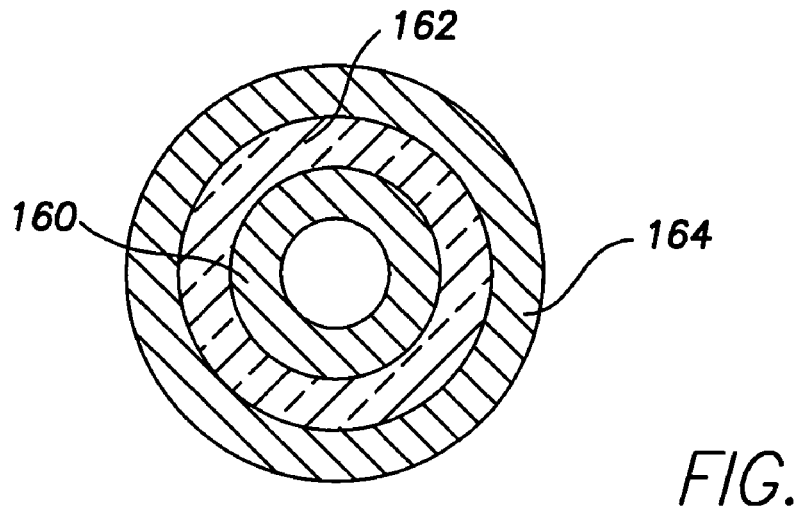
FIG. 7 is a cross-sectional view of a lead that may be implanted in a left ventricle.

Referring now to FIG. 7, it shows one possible cross section of lead 24. Here, the lead includes a central stylet coil 160 of the type well known in the art for providing the electrical connection from the output 73 of the left ventricular pulse generator to the electrode 26. Overlying the stylet coil 160 is a layer of insulation 162. The insulation 162 may, for example, be silicon rubber. To prevent the exposed silicon rubber insulation from promoting thrombosis, the lead of FIG. 7 further includes a conductive coating 164. The conductive coating 164 preferably covers all of the insulation 162. The conductive coating 164 may then be coupled to the power supply circuit 112 to maintain the coating 164 at a negative voltage to enable the conductive coating 164 to repulse blood cells and hence forestall thrombosis.

Figure 8:
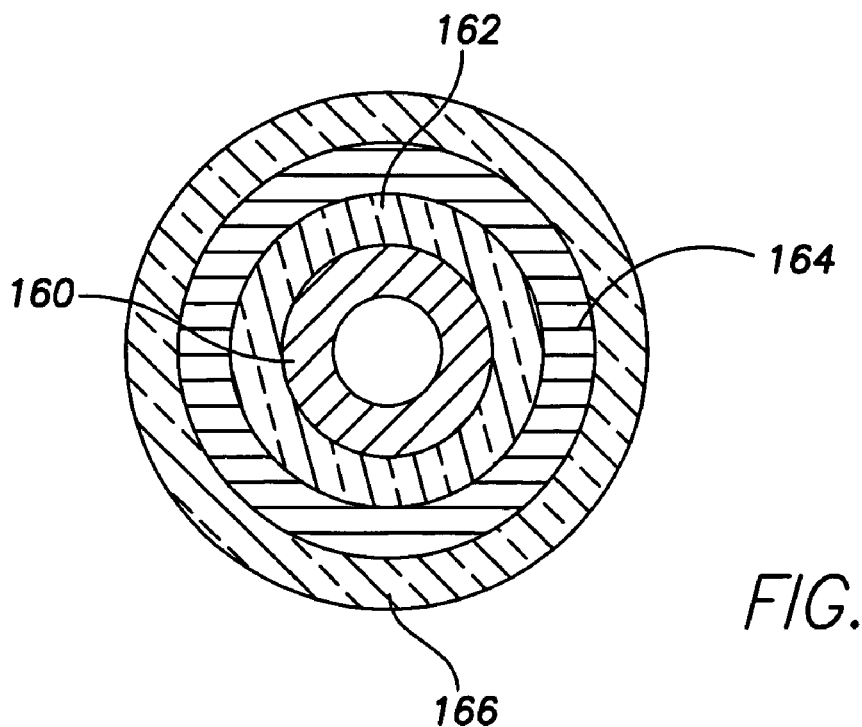
FIG. 8 is a cross-sectional view of another implantable lead.

FIG. 8 shows a cross section of another lead. Like the cross section illustrated in FIG. 7, the lead of FIG. 8 includes the stylet coil 160, the silicon rubber insulation 162, and the conductive coating 164. Overlying the conductive coating 164 is a further insulating layer 166 which may also be formed of silicon rubber, for example. In order to prevent the silicon rubber layer 166 from promoting thrombosis formation, the conductive coating 164 may be coupled to the power supply circuit 112 of the device 10 to repel blood cells. Since the conductive coating 164 is acting through the insulating layer 166, the voltage required to repel the blood cells will be higher in this embodiment, than in the previous embodiment of FIG. 7. For example, a −100 volts may be applied to the conductive coating 164 to repel blood cells sufficiently to preclude the insulative layer 166 from promoting thrombosis. Such voltage levels are readily obtainable from the power supply circuit 112 in a manner well known in the art as such voltage levels are customarily developed in such devices.

From the foregoing it may be seen that the implantable cardiac stimulation device is capable of providing pacing therapy from within the left ventricle while preventing thrombosis which may otherwise potentially result from such an arrangement. In accordance with the broader aspects of the illustrative embodiments, the pacing electrode within the left ventricular blood pool is maintained at a negative voltage to repel blood cells and forestall thrombosis. The remaining portions of the lead exposed to the blood pool of the left ventricle are also precluded from causing thrombosis by the application of a negative voltage to an electrically conductive coating. The electrically conductive coating may be directly exposed to the left ventricular blood pool or may be separated therefrom by an insulative layer. The conductive coating is preferably coupled to a second power supply circuit for receiving its negative voltage to repel the blood cells within the left ventricle.

While specific embodiments and applications have been described, it is understood that numerous modifications and variations may be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation system comprising:
at least one implantable lead including at least one stimulation electrode; and
an implantable cardiac stimulation device comprising a pulse generator adapted to be coupled to the at least one stimulation electrode, and a first power supply, adapted to be selectively coupled to an output of the pulse generator, that substantially continuously maintains the at least one stimulation electrode at a first negative voltage, wherein the pulse generator provides the pacing pulses to the stimulation electrode and wherein the lead includes a conductor that couples the pulse generator and the power supply to the at least one electrode, an insulator overlying the conductor, a conductive coating overlying the insulator, and a second insulator overlying the conductive coating, and wherein the device includes a second power supply coupled to the conductive coating that maintains the conductive coating at a second negative voltage.

2. The system of claim 1 wherein the pulse generator and the first power supply together provide less than an average current of 100 nano amperes to the stimulation electrode.

3. The system of claim 1 wherein the pulse generator provides a negative going stimulation pulse starting from the first negative voltage.

4. The system of claim 1 wherein the pulse generator provides a positive going stimulation pulse starting from the first negative voltage.

5. The system of claim 1 wherein the absolute value of the first negative voltage applied to the stimulation electrode is greater than 25 mV.

6. The system of claim 5 wherein the first negative voltage applied to the stimulation electrode is on the order of 50 mV.

* * * * *